United States Patent [19]

Batz et al.

[11] 4,155,914
[45] May 22, 1979

[54] HYDROXY-SUCCINIMIDE ESTER COMPOUNDS

[75] Inventors: Hans-Georg Batz, Tutzing; Jürgen Horn, Tutzing-Garatshausen; Klaus Stellner, Bernried; Josef Maier, Weilheim; Michael Nelboeck-Hochstetter; Gunter Weimann, both of Tutzing, all of Fed. Rep. of Germany

[73] Assignee: Boehringer Mannheim GmbH, Mannheim-Waldhof, Fed. Rep. of Germany

[21] Appl. No.: 815,338

[22] Filed: Jul. 13, 1977

[30] Foreign Application Priority Data

Jul. 14, 1976 [DE] Fed. Rep. of Germany ....... 2631656

[51] Int. Cl.$^2$ .................... C07D 207/46; C07G 7/00
[52] U.S. Cl. .................... 260/326.4; 260/326.26; 260/112 R; 260/112.5 R
[58] Field of Search ........................ 260/326.4

[56] References Cited

U.S. PATENT DOCUMENTS 3,996,268  12/1976  Carpenter et al. ............... 260/479 S
4,064,270  12/1977  Wollweber et al. ............... 242/324

FOREIGN PATENT DOCUMENTS 2263472  1/1972  Fed. Rep. of Germany.
2525058  12/1975  Fed. Rep. of Germany.

OTHER PUBLICATIONS

Moroder et al., Chemical Abstracts, vol. 79, 19100k, (1973).
Winston et al., Chemical Abstracts, vol. 84, 5419n, (1976).

Primary Examiner—Donald G. Daus
Assistant Examiner—Diana G. Rivers
Attorney, Agent, or Firm—Sprung, Felfe, Horn, Lynch & Kramer

[57] ABSTRACT

New hydroxy-succinimide ester compounds of the formula

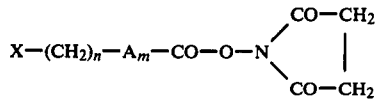

wherein
X is selected from a carboxy-succinimide ester group and radicals of the general formulae:

$-CO-NH-CH_2-CH(OR')_2$

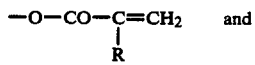 and

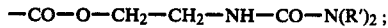

A is $-O-CH_2-CH_2$ when n is 2 and X is a succinimide ester group but otherwise is a single bond;
n is a whole number of from 2 to 7;
m is 1, 2, 3 or 4;
R is hydrogen, methyl, or cyanide; and
R' is methyl or ethyl;

have been found outstandingly useful as bridge-building compounds for linking proteins, especially biologically active proteins, to solid or liquid carrier matrix materials, thereby yielding valuable carrier-bound enzymatically active protein compositions.

4 Claims, No Drawings

HYDROXY-SUCCINIMIDE ESTER COMPOUNDS

The present invention relates to new hydroxy-succinimide ester compounds and to the preparation thereof. An additional aspect of the invention relates to the use of such compounds for the production of covalent bondings of proteins, especially of biologically active proteins, to prepare cross-linking or carrier fixed protein compositions.

The interest in immobilized, and especially in carrier-bound, enzymatically active proteins is continuously increasing. Several processes for the covalent bonding of proteins with carrier substances are already known, for example from German Patent Specifications Nos. 2,128,743 and 2,260,185. Immobilized enzymes are particularly important because they result in the stabilization of biologically active materials and make possible their separation from aqueous reaction media.

In the first processes for the covalent bonding of biologically active proteins, activating groups were introduced into the carrier matrix. An important disadvantage of these known methods is the low activity yield, which was attributed to the adverse effect of the carrier matrix on the active configuration of the protein, due to the close proximity thereof. Attempts were, therefore, made to overcome this disadvantage by introducing bridge members between the protein and the carrier.

These bridge members are derived from so-called bridge building compounds, which are usually homo- or hetero-difunctional compounds having a function which reacts with the protein in aqueous solution, leading to the formation of a covalent bond, and having a further function capable of forming a bond with the carrier. In the case of homodifunctional bridge builders, such as glutardialdehyde or diepoxides, the two functional groups are the same.

Therefore, protein and carrier are reacted simultaneously, there taking place not only a protein cross-linking but also a bonding with the carrier at the same time. Processes have proved to be favorable in which a two-stage method of working is used, with bonding of the bridge building molecule first with the protein or with the carrier and subsequently with the carrier or with the protein, respectively. For these processes, it has proved to be preferable to use heterodifunctional bridge building compounds with two different functional groups of different reactivity.

Furthermore, it is known first to adsorb the proteins physically on the surface of appropriate carriers and then to fix them on these surfaces by cross-linking with polyfunctional bridge builders.

In all of these known processes, it has been found that different bridge building compounds behave in a different manner, depending upon the protein to be bound and upon the carrier material to be used, greatly varying results being obtained. Therefore, in practice, for each particular case of protein immobilization, the most favorable bridge building substance has to be found. Especially good bridge builders for some cases have thereby proved to be completely unsatisfactory for other cases. In many cases, a satisfactory covalent bonding of active proteins has hitherto been completely unsuccessful.

Thus, there is still a need for further bridge building compounds which provide a further possibility for the covalent bonding of biologically active proteins and especially of enzymes. In particular, there is a need for bridge building compounds which can be homodifunctional or heterodifunctional and which contain functional groups reacting especially quickly and gently with proteins, the distance between the functional groups being so great that conformation changes of the bound protein due to the carrier are substantially excluded and in which the "bridge" which joins the two functional groups can, if desired, be varied with regard to its hydrophobic or hydrophilic properties. It is an object of the present invention to provide such compounds.

Thus, according to the present invention, there are provided hydroxy-succinimide ester compounds of the formula

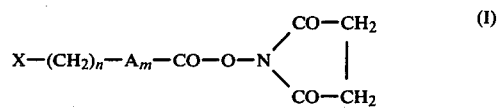

wherein X is a further carboxy-succinimide ester radical or a radical of the formula

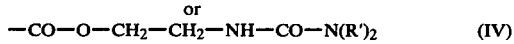

A is a —O—CH$_2$—CH$_2$— radical when n is 2 and X is a further carboxy-succinimide ester group but otherwise is a single bond, n is a whole number of from 3 to 7, m is 1, 2, 3 or 4, R is a hydrogen atom or a methyl or cyanide radical and R' a methyl or ethyl radical.

Depending upon the nature of the residue X, the new compounds (I) are either homodifunctional or heterodifunctional compounds. By variation of m and n, the hydrophobic or hydrophilic properties of the bridge can be "tailor made", the hydrophobic properties increasing when n is greater and the hydrophilic properties increasing when m is greater. If cross-linking of the proteins is desired, the homodifunctional compounds of the present invention are preferred, whereas when a bonding with a solid or liquid carrier material is desired, the heterodifunctional compounds are preferred in which X is a radical of the formulae (II), (II) or (IV). If bonding with the carrier takes place by copolymerization, then compounds are especially preferred in which X is a radical of the general formula (III). The hydroxy-succinimide ester group (HOSu residue) reacts selectively in aqueous solution with amines and is, therefore, especially useful for the covalent bonding of proteins.

According to the present invention, the new compounds of general formula (I) can be prepared from the mono- or dicarboxylic acid upon which the hydroxy-succinimide esters are based by either (a) converting the acid in known manner into a reactive derivative, such as an acid chloride or mixed anhydride, and reacting the reactive derivative in an organic solvent with N-hydroxy-succinimide, or (b) condensing the acid directly, in a polar organic organic solvent, with N-hydroxy-succinimide in the presence of an amount of cyclohexylcarbodiimide equivalent to the latter, or (c) reacting the acid in the form of an alkali metal salt with N-hydroxy-succinimide-methyl sulphonate in the presence of a crown compound as catalyst.

The preparation of the compounds (I) via a mixed anhydride in organic solvent, for example methylene chloride, furan, dioxan or the like, proves, in many cases, to be the simplest and best method. The reactive acid derivative used is preferably a mixed anhydride with chloroformic acid.

Preferred carrier substances for use with the new compounds according to the present invention for the covalent bonding of proteins include not only water-soluble but also water-insoluble, solid or liquid substances which are able to react with the functional groups represented by X, the reactive groups thereby preferably being hydroxy or amino groups.

The carrier substances preferably used include those which are hydrophilic, easily swellable and substantially charge-free, as well as stable towards microorganisms.

According to a preferred process, the compounds according to the present invention, when X is a radical of the general formula (III), are bonded by copolymerization with a carrier which is prepared in situ by polymerization of appropriate monomers or monomer mixtures or are incorporated directly into a carrier by copolymerization with appropriate comonomers.

The copolymerizable monomer used in this case can be water-soluble or water-insoluble. Water-soluble monomers are preferred when the coupling compound according to the present invention has first been reacted with a biologically active protein and is thereafter to be fixed on to a carrier in homogeneous aqueous solution, which carrier has been formed in situ by copolymerization. Instead of this, it is also possible to use suspension or emulsion polymerization methods in which the coupling product of a protein with a compound of the general formula (I) according to the present invention is present in the aqueous dispersed phase and a water-insoluble monomer or monomer mixture represents the dispersed phase. Especially preferred comonomers include water-soluble and water-insoluble derivatives of acrylic acid and methacrylic acid, for example the amides, nitriles and esters of these compounds. Among the water-soluble comonomers, acrylamide is preferred. Water-insoluble derivatives of acrylic acid or methacrylic acid, especially those which are substituted by alkyl radicals, are preferred when the carrier-bound protein is subsequently to be used in an aqueous organic medium rather than in a purely aqueous system. Other appropriate monomers are derived, for example, from maleic or fumaric acid. However, the monomers which can be used are not limited to those mentioned here by way of example.

As monomers, there can also be employed prepolymers which still contain unsaturated, copolymerizable groups.

In order to regulate the physical properties in the case of carriers produced in this manner by copolymerization, appropriate cross-linkers are preferably added in appropriate amounts. Such cross-linkers include compounds with at least two copolymerizable groups, for example N,N'-methylene-bis-acrylamide and ethylene diacrylate. However, radical-acting cross-linkers, for example certain organic peroxides, can also be employed.

When carrying out the polymerization in the heterogenous phase, i.e. by suspension or emulsion polymerization, there can be used, for example, water-insoluble cross-linkers, such as divinylbenzene or ethylene dimethacrylate. Numerous other cross-linkers are known and the appropriate choice in a particular case can readily be made. It is, however, also possible subsequently to introduce the cross-linker and to carry out the cross-linking after the preparation of the polymeric carrier and the bonding with the active protein has taken place.

If the polymer formed is not cross-linked, then soluble or thermoplastic materials are obtained. These can be used for spinnable or extrudable solutions from which the carrier bound proteins can be obtained in known manner, for example in the form of filaments or foils.

For coupling with hydroxyl group-containing carrier substances, it is especially preferred to use those compounds of general formula (I) in which X is a radical of general formula (IV). Thus, this radical forms, upon heating to about 100° C. in an organic solvent, for example dimethyl sulphoxide, by splitting off diethylamine, the corresponding isocyanate of the formula:

$$-N=C=O \qquad \text{(IVa)}$$

which reacts at 0° C. with hydroxyl groups. Under these conditions, the hydroxy-succinimide ester group (OSu ester) does not react so that a selective reaction of the two functional groups of the molecule is possible by reaction under the conditions appropriate in each case.

The compounds of general formula (I), in which X is a radical of general formula (II), are first reacted via the HOSu radical with an amino group-containing low or high molecular weight substance and subsequently further reacted in a weakly acidic aqueous solution. Under these conditions, from the acetal there is formed the free aldehyde which then further reacts in known manner with, for example, amino groups with the formation of a Schiffs base which is thereafter reduced with, for example, sodium borohydride, to form a covalent bond. In an analogous manner, there can also be used hydroxylamine, hydrazine or a semicarbazide derivative.

Furthermore, as carriers there can also be used those solid substances which have no positions reactive with the functional groups of the compounds according to the present invention. In such cases, the compounds according to the present invention are used as cross-linkers. The active protein is hereby preferably first applied to the surface of the carrier body, for example by adsorption, coating with a solution of the protein or the like, followed by anchoring on to this surface by cross-linking with a compound according to the present invention, the homodifunctional derivatives preferably being used, i.e. those compounds in which X is a further carboxy-succinimide ester radical. However, compounds in which X is a radical of general formula (IV) can also be used for the cross-linking.

In a further preferred method of using the new compounds according to the present invention, a biologically active protein is reacted not only with a homodifunctional but also with a heterodifunctional compound of general formula (I). For example, a protein is first reacted with a compound in which X is a radical of general formula (III), which leads to the introduction of copolymerizable residues. Subsequently, a cross-linkable and preferably a homodifunctional compound is added thereto in which X is a further carboxysuccinimide ester group. This leads to a cross-linking, several molecules thus being linked with one another. This complex body, consisting of several protein units, can then, as described above, be immobilized on a carrier by means of the copolymerizable residues present therein, according to the above-described methods of protein copolymerization. In the same way, it is also possible, instead of a copolymerizable group, to introduce a radical of the general formula (II) or (IV) according to this method and to produce the bonding with a preformed carrier.

According to a further variant, the protein is first cross-linked, with the bonding together of several protein molecules, followed by immobilization on a carrier with the same or with a different compound of general formula (I).

Biologically active proteins which can be covalently bound with the compounds according to the present invention include enzymatically active proteins and immunologically active proteins, such as antibodies, immunoglobins and the like, as well as hormone-active proteins.

The new compounds according to the present invention are characterized by their reactivity with proteins which, in aqueous or aqueous-organic solution, leads to the formation of covalent bonds with the substantial maintenance of the biological activity, as well as by their reactivity with copolymerizable double bonds, hydroxyl groups and amino groups and also with other active groups present in the carrier substances for proteins. A further advantage of these new esters is that they crystallize well and can, therefore, easily be isolated in pure form. They can form covalent bondings with carriers under conditions in which the biological activity of the proteins remains intact. Furthermore, their hydrophilic or hydrophobic properties can easily be varied, as desired. Thus, for example, symmetrical bis-hydroxy-succinimide esters can be added in the particular appropriate amount to a solution of a protein in a weakly alkaline buffer. The cross-linked biologically active proteins thereby obtained can either be separated off, for example by dialysis, ultrafiltration or the like, or can be separated off, for example by gel chromatography, or can be further reacted, for example by bonding on to a carrier or polymerizing into one. The compounds according to the present invention derived from ethylene glycol are thereby superior to simple dicarboxylic acid hydroxy-succinimide esters because of their hydrophilic properties. Because of their better water solubility, they react more quickly and denaturing of biologically active proteins is suppressed.

In the case of the asymmetrical (heterodifunctional) compounds, it is, for example, possible to convert the amido-acetaldehyde-acetal group, after coupling of the hydroxy-succinimide group with a protein, into the free aldehyde by acidification, followed, as described above, by reaction with a further amino group-containing substance.

Therefore, it is possible to couple, for example, not only two different enzymes with one another, but also an enzyme on to albumin or an antigen on to bovine serum albumin or on to a polyamino acid, such as polyamine.

The compounds containing a copolymerizable double bond can be used, for example, according to the methods described in German Patent Specifications Nos. 2,130,913 and 2,128,743, for protein copolymerization. It is also possible first to subject these compounds to a copolymerization, whereby, depending upon the choice of the comonomers, readily or less-readily water-soluble copolymers are obtained. Proteins can then be coupled on to these copolymers, which can be prepared with any desired molecular weight, via the hydroxy-succinimide ester group.

The following Examples are given for the purpose of illustrating the present invention:

EXAMPLE 1

Ethylene glycol-bis-propionic acid bis-hydroxy-succinimide ester

To a solution of 10.3 g. ethylene glycol bis-propionic acid (prepared according to the method of R. V. Christian and R. M. Hixon, J.A.C.S., 70, 1333/1948; Doc. No. 12916) and of 12.6 g. N-hydroxy-succinimide in 150 ml. anhydrous tetrahydrofuran, there is added dropwise, with stirring and ice cooling, over the course of one hour, a solution of 22.7 g. dicyclhexyl carbodiimide in tetrahydrofuran. The solution is stirred for 18 hours at ambient temperature. 0.3 ml. acetic acid are then added thereto. After a further hour, 150 ml. anhydrous ethyl acetate are added thereto and precipitated dicyclohexylurea is filtered off. The filtrate is concentrated to one third, washed with water, aqueous sodium bicarbonate solution and again with water, dried over anhydrous sodium sulphate and evaporated. The residue is taken up in acetonitrile, left to stand for 24 hours at $+4°$ C., then filtered off from freshly precipitated urea and again evaporated. After standing for several days at $+4°$ C., the desired product thus obtained crystallizes out from the residual oil. It is recrystallized from ethyl acetate; yield: 25% of theory; m.p. 115° C.

Analysis: $C_{16}H_{20}N_2O_{10}$ (M.W. 400.35) calculated: C, 47.99%; H, 5.04%; N, 6.99%. Found: C, 47.95%; H, 5.04%; N, 6.87%.

EXAMPLE 2

In a manner analogous to that described in Example 1, there is prepared oxy-bis-propionic acid hydroxysuccinimide ester; yield: 30% of theory; m.p.: 131° C.

EXAMPLE 3

Oxy-succinimide-glutaric acid aminoacetaldehyde dimethylacetal

To a solution of 11.4 g. glutaric acid anhydride in 100 ml. tetrahydrofuran there is simultaneously dropped in 10.1 g. triethylamine and 13.2 g. aminoacetaldehyde dimethylacetal, whereafter the reaction mixture is stirred for 30 minutes. The resultant solution is cooled to $+5°$ C. and slowly mixed with 9.5 ml. ethyl chloroformate. The reaction mixture is then kept for 30 minutes at $-5°$ C. Subsequently, 11.5 g. hydroxysuccinimide and 14.0 ml. triethylamine are simultaneously added dropwise at 0° C. After reaction for 5 hours at $+25°$ C., precipitated triethyl ammonium chloride is filtered off, the filtrate is evaporated and the residue is again taken up in ethyl acetate, washed with water, aqueous sodium bicarbonate solution and again with water, dried over anhydrous sodium sulphate and evaporated. The desired product thus obtained is recrystallized from hot ethyl acetate; yield: 45% of theory; m.p.: 70° C.

Analysis: $C_{13}H_{20}N_2O_7$ (M.W. 316.3) calculated: C, 49.60%; H, 6.38%; N, 8.85%. Found: C, 49.34%; H, 6.37%; N, 8.81%.

EXAMPLE 4

Methacryloxyl-ω-hydroxy-carboxylic acid hydroxysuccinimide ester

The methacryloxyl-ω-hydroxycarboxylic acids are prepared in a manner analogous to the process described in Makromol. Chem., 176, 3017/1973). In a 500 ml. three-necked flask are placed 0.1 mol of the methacryloylhydroxy acid in question and 0.11 mol N-hydroxysuccinimide in a mixture of anhydrous methylene chloride and anhydrous methylene chloride and anhydrous tetrahydrofuran and then cooled in an ice-bath to +5° C. A solution of 0.11 mol dicyclohexylcarbodiimide, dissolved in 50 ml. anhydrous methylene chloride, is added dropwise thereto, while stirring. The reaction mixture is further stirred for about 12 hours, the temperature thereby increasing to +25° C. Precipitated dicyclohexylurea is thereafter filtered off and the filtrate is evaporated. The resulting oil is taken up in acetonitrile and left to stand for several hours in a refrigerator. Further precipitated urea is filtered off and the acetonitrile is evaporated off from the filtrate. The product is thus obtained in the form of an oil.

EXAMPLE 5

Hydroxysuccinimido-N-2-hydroxyethyl-N-',N'-dimethylurea succinic acid ester 13.2 g. N-2-hydroxyethyl-N',N'-dimethylurea are dissolved in anhydrous tetrahydrofuran. 2.4 g. of a sodium hydride suspension are then added dropwise in the course of about 5 minutes. The reaction mixture is stirred at ambient temperature until the evolution of hydrogen has ceased, whereafter 10 g. succinic anhydride are added thereto. After stirring for a further 24 hours, the reaction mixture is evaporated and water is added thereto. After the evolution of hydrogen has ceased, the organic components are separated off and the solution is acidified and shaken out with methylene chloride. The organic phase is dried and evaporated, a pale yellow oil remaining behind; yield: 53% of theory.

The hydroxysuccinimide ester was prepared from this acid in a manner analogous to that described in Example 4; yield: 35% of theory; m.p.: 97°–98° C.

Analysis: calc.: C, 47.5%; H, 5.8%; C, 12.8%. Found: C, 47.5%; H, 5.8%; C, 12.8%.

By heating to about 100° C. in dimethyl sulphoxide, diethylamine is split off with the formation of the corresponding isocyanate.

The following Examples illustrate the use of the new compounds according to the present invention:

EXAMPLE 6

Stabilization of trypsin by cross-linking with various symmetrical bifunctional compounds.
Comparative experiment.

In a first experiment, trypsin was reacted with glutaraldehyde and, in a second experiment, with suberic acid bis-imido ester hydrochloride, the decrease of activity of the thus cross-linked trypsin being compared with that of free trypsin. To 50 mg. amounts of trypsin in 25 ml. distilled water, there were added 2 μM of the cross-linker substance, dissolved in 0.05 M phosphate buffer (pH 7.5), followed by stirring at ambient temperature. After 20 hours, the activity of the free trypsin, as well as of the trypsin cross-linked with glutaraldehyde, had dropped to 15% of the initial activity. After 50 hours, the activity in all three samples had dropped to 0. The trypsin cross-linked with suberic acid bis-imido ester hydrochloride still had, after 50 hours, 50%, after 50 hours still 30% and after 100 hours still 20% of the initial activity.

The experiment was repeated with the esters of Examples 2, 3 and 4 according to the present invention. After 20 hours, the activity with the compound of Example 3 was still 85% and with that of Example 4 still 50%. After 50 hours, the activity of the trypsin cross-linked with the compound of Example 2 was 43% and with the compound of Example 3 was 27%. After 100 hours, with the compound of Example 2, an activity of 25% was measured. This Example 6 shows the superiority of the compounds according to the present invention, in comparison with known cross-linking agents.

EXAMPLE 7

Stabilization of kidney acylase by cross-linking.

The activity of kidney acylase in 0.1 M phosphate buffer (pH 4) drops, in spite of cooling to 4° C., within 3 to 5 days to 0. If, however, the compound of Example 1 or suberic acid bis-hydroxysuccinimide ester (prepared analogously to Example 1) is added thereto, then an initial drop of activity takes place to 70 to 50%. This remaining activity was monitored for 2 months and remained constant over this period of time. This result is always achieved in the case of variation of the mol ratio of protein to ester of from 1:1 to 1:8.

A comparative experiment with glutaraldehyde instead of the bis-ester according to the present invention does not lead to any stabilization.

EXAMPLE 8

Immobilization of kidney acylase by copolymerization.

1000 mg. aminoacylase (lyophilisate) (specific activity 17.0 U/mg.) are dissolved in 25.0 ml. 1 M tris buffer (pH 8.3) at +4° C. To this are added 2.5 ml. of a solution of 30.7 mg. methacrylic hydroxycapronic acid hydroxysuccinimide ester (see Example 4) in dioxan. The reaction time is 12 hours at +4° C.

6 g. Acrylamide, 0.5 g. N,N'-methylene-bis-acrylamide and 0.6 ml. of a 1% cobalt chloride solution are dissolved in 22.5 ml. of the above tris buffer. After the addition of the vinylated enzyme solution, polymerization is started with 1.5 ml. each of a 5% ammonium peroxydisulphate solution and of a 5% 3-dimethylaminopropionitrile solution. The resultant gel is pressed through a sieve (mesh size 0.4 mm.) and eluted in a column with 1 M phosphate buffer (pH 7.5).

1st eluate: 2 liters buffer 1.88% activity in eluate; specific activity on the gel 193.1 U/g.

2nd eluate: 2 liters buffer—specific activity on the gel 193.1 U/g.

Activity yield: 6.9%.

The Example was repeated with the use of acryloyl chloride instead of the compound according to the present invention: no activity was bound on to the carrier.

EXAMPLE 9

Immobilization of glucose oxidase (GOD) by a 2 stage reaction with compounds according to the present invention and subsequent copolymerization.

As described in Example 8, GOD with a specific activity of about 210 U/mg. was pre-incubated with the compound of Example 4 and subsequently a small amount of the compound of Example 1 was added thereto. Thereafter, the reaction mixture was left to stand for a further 24 hours and subsequently copolymerization was carried out in the manner described in Example 8. An activity of 290 U/g. was measured in the gel obtained.

A repetition of this experiment with the use of acryloyl chloride instead of the compounds according to the present invention gave an activity of 235 U/g.

EXAMPLE 10

Coupling of angiotensin on to BSA (bovine serum albumin).

25 mg. angiotensin were dissolved in 10 ml. dioxan/water (1:1 v/v) and mixed with a solution of 6 mg. of the compound of Example 4 in dioxan. The pH value was then brought to 8.0 by the addition of 5% aqueous potassium carbonate solution and stirred for 2 days at ambient temperature. The product was precipitated out by the addition of tetrahydrofuran, centrifuged off and lyophilised; yield: 19.6 mg. of theory.

The 19.6 mg. of this intermediate were adjusted to pH 4 and stirred for 1 hour. Subsequently, the pH value was again adjusted to 8.0 and the solution mixed with 16.6 mg. BSA. After stirring for one hour, the reaction mixture was mixed with 1 mg. sodium borohydride. After a further 20 minutes, a further 1 mg. sodium borohydride was added. After a further 60 minutes, the reaction was finished. The solution was evaporated and the residue was taken up in absolute ethanol, filtered, water added thereto and then dialysed for 4 days. From the dialysate there were obtained 24.1 mg. lyophilisate. From this it follows that at least 24 molecules angiotensin are coupled with 1 molecule BSA.

EXAMPLE 11

Copolymerization of the ω-methacrylol-hydroxycarboxylic acid-hydroxysuccinimide esters with methacrylamide.

There was prepared an oxygen-free solution (1 mol/dm³) of the two monomers in anhydrous tetrahydrofuran (monomer ratio ester:amide=1:5). Polymerization took place by the addition of 0.8% (mol/mol) azoisobutyric acid dinitrile at 58° C. After 4 hours, polymerization was discontinued by cooling (dipping into an ice-bath) and the precipitated polymer was filtered off with suction. It was again dissolved in water and reprecipitated by dropping the aqueous solution into acetone.

It will be understood that the specification and examples are illustrative but not limitative of the present invention and that other embodiments within the spirit and scope of the invention will suggest themselves to those skilled in the art.

What is claimed is:

1. Hydroxy-succinimide ester compound of the formula

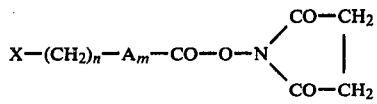

wherein
X is

A is a single bond;
n is a whole number of from 2 to 7; and
R' is methyl or ethyl.

2. Hydroxy-succinimide ester compound as claimed in claim 1 wherein R' is methyl.

3. Hydroxy-succinimide ester compound as claimed in claim 1 wherein R' is ethyl.

4. Hydroxy-succinimide ester compound as claimed in claim 1 designated oxy-succinimide-glutaric acid aminoacetaldehyde dimethyl acetal.

* * * * *